(12) United States Patent
Theodorsen

(10) Patent No.: US 9,285,348 B2
(45) Date of Patent: Mar. 15, 2016

(54) AUTOMATED SYSTEM FOR HANDLING COMPONENTS OF A CHROMATOGRAPHIC SYSTEM

(71) Applicant: Proxeon Biosystems A/S, Odense C (DK)

(72) Inventor: Soeren Theodorsen, Odense (DK)

(73) Assignee: Proxeon Biosystems A/S, Odense C (DK)

( * ) Notice: Subject to any disclaimer, the term of this patent is extended or adjusted under 35 U.S.C. 154(b) by 324 days.

(21) Appl. No.: 14/068,104

(22) Filed: Oct. 31, 2013

(65) Prior Publication Data

US 2014/0338430 A1    Nov. 20, 2014

(51) Int. Cl.
| | |
|---|---|
| *G01N 30/08* | (2006.01) |
| *G01N 30/24* | (2006.01) |
| *G01N 35/00* | (2006.01) |
| *G01N 35/10* | (2006.01) |

(52) U.S. Cl.
CPC ............... *G01N 30/08* (2013.01); *G01N 30/24* (2013.01); *G01N 35/0099* (2013.01); *G01N 2030/085* (2013.01); *G01N 2035/1013* (2013.01)

(58) Field of Classification Search
CPC ... G01N 30/08; G01N 30/24; G01N 35/0099; G01N 2030/085
USPC .......................................................... 73/293
See application file for complete search history.

(56) References Cited

U.S. PATENT DOCUMENTS

| | | | | |
|---|---|---|---|---|
| 4,705,081 A * | 11/1987 | Birk | ...................... | H05K 13/023 140/147 |
| 5,260,028 A | 11/1993 | Astle | | |
| 5,443,791 A * | 8/1995 | Cathcart | ............ | G01N 35/0098 422/561 |
| 5,559,727 A * | 9/1996 | Deley | ................. | H05K 13/0413 356/400 |
| 5,660,792 A | 8/1997 | Koike | | |
| 2006/0048846 A1 * | 3/2006 | Roenneburg | ........... | G01N 30/88 141/130 |
| 2007/0175757 A1 * | 8/2007 | Hanafusa | ................. | C07K 1/26 204/451 |
| 2008/0047368 A1 * | 2/2008 | Marziali | .............. | B01J 19/0046 73/863 |
| 2008/0287661 A1 * | 11/2008 | Jones | .................... | B01L 3/0275 530/418 |
| 2012/0121464 A1 | 5/2012 | Nogami et al. | | |

* cited by examiner

*Primary Examiner* — Peter Macchiarolo
*Assistant Examiner* — Nathaniel Kolb
(74) *Attorney, Agent, or Firm* — Charles B. Katz

(57) ABSTRACT

An automated system for handling components of a chromatographic system, comprising: one or more trap columns each having sorbent material therein; a robotic system for moving a trap column from a storage position to an operating position where the trap column is connected in a liquid pathway along which solvent is flowed in operation to a liquid chromatography (LC) column; and an optical sensor for sensing one or more parameters of the trap column. Sensed parameters can include: a presence or absence of a trap column in the operating position, a position or orientation of the trap column, a fluid level in the trap column, the presence and position of a sorbent material in the trap column, the condition of the trap column and/or whether the trap column is new or used.

18 Claims, 6 Drawing Sheets

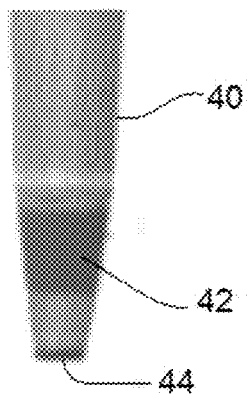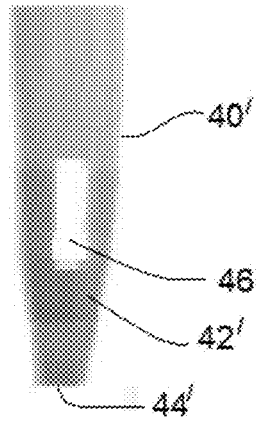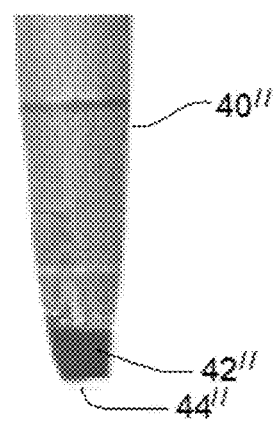
Fig. 5A       Fig. 5B       Fig. 5C
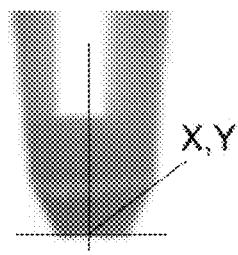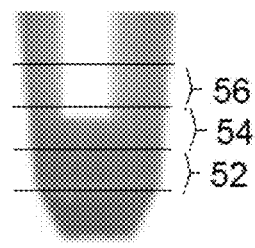
Fig. 6A       Fig. 6B

AUTOMATED SYSTEM FOR HANDLING COMPONENTS OF A CHROMATOGRAPHIC SYSTEM

FIELD OF THE INVENTION

The present invention relates to the field of chromatographic systems and particularly automated systems for handling components of a chromatographic system.

BACKGROUND OF THE INVENTION

Mass spectrometry (MS) is an established method for the analysis of many biochemical samples such as, for example, protein and peptide samples in proteomics research. Whilst MS may be used directly on simple samples, in cases of complex samples consisting of a large number (possibly thousands) of components (e.g. proteins), the samples are typically subject to a separation process prior to the MS analysis, e.g. by liquid chromatography (LC). Prior to the LC process of the LC/MS analysis, a sample preparation is often performed that may involve some form of sample separation, such as a purification and/or concentration step.

Solid phase extraction (SPE) is a technique for preparing samples prior to LC. The technique comprises using a sorbent held in a column commonly known as a trap column, often in the form of a disposable cartridge or tip, to purify and/or concentrate samples prior to analysis. Disposable SPE cartridges or tips that can be disposed of after a single use have the advantage that they avoid a step of cleaning them before the next use. The use of SPE followed by LC is herein termed an SPE-LC method.

Attempts have been made to increase throughput in SPE-LC by using an automated system to interface the SPE columns to the LC system. Such systems are described in U.S. Pat. No. 7,409,880 and Hørning et al, International Journal of Mass Spectrometry 268 (2007) 147-157. A multiplicity of SPE tips are held in a rack, typically with sample pre-loaded onto the tips, and a robotic system moves the tips from the rack to a receiver connected to the head of the LC column. A capillary or other solvent delivery member is positioned in a first open end of the tip and the second open end of the tip makes a seal with the receiver such that in operation a solvent is flowed by means of a pumping system in a fluid-tight manner from the capillary through the tip to transport sample from the sorbent downstream to the LC column.

A problem with such automated systems is that they are not completely reliable and robust. For example, it is possible for the robotic system to fail to pick up a tip, or fail to pick up a tip correctly. In addition, it is possible that a tip that has been picked up may be dropped before it is connected to the LC system. Sometimes the automated system may use a tip that is damaged or otherwise unfit for use, for example since it has already been used. Attempted use of the system when such events occur may cause damage to the system or at least lead to spurious results. An aim of the invention is to address such problems.

SUMMARY OF THE INVENTION

According to an aspect of the present invention there is provided an automated system for handling components of a chromatographic system, comprising:

one or more trap columns each having sorbent material therein;

a robotic system for moving a trap column from a storage position to an operating position where the trap column is connected in a liquid pathway along which solvent is flowed in operation to a liquid chromatography (LC) column; and an optical sensor for sensing one or more parameters of the trap column.

According to another aspect of the present invention there is provided a method of automatically handling components of a chromatographic system, comprising:

using a robotic system to move a trap column having sorbent material therein from a storage position to an operating position where the trap column is connected in a liquid pathway along which solvent is flowed in operation to a liquid chromatography (LC) column; and sensing one or more parameters of the trap column using an optical sensor.

Preferably, the optical sensor enables an image of the trap column to be produced. Numerous parameters of the column may be determined from the image. The invention provides a non-contact method of determining one or more parameters of the trap column and can perform the determination more quickly, reliably and accurately than performing the task manually.

Using the sensor it is possible to determine numerous parameters of the trap column, such as the presence or absence of a trap column at the location of the sensor (preferably the operating position) (e.g. whether a column has been picked up by the robotic system or not, or has been dropped by the robotic system), the position or orientation of the trap column (e.g. whether a column has been picked up correctly and/or is at the correct orientation in the robotic system), the presence and position of a sorbent material in the trap column, a fluid level in the trap column, the condition of the column (e.g. whether any damage to the column has occurred) and/or whether the trap column is new or used. These parameters may be sensed before an analysis is performed thereby to avoid possible damage to the system or to avoid obtaining spurious results if defects in the parameters are found. If an analysis is performed, the sensing of the parameters may be used to determine whether results of the analysis should be treated as spurious, e.g. if defects are found in one or more of the parameters. This ensures that the system is reliable and robust.

Additional aspects and preferred embodiments and implementations of the invention are further described below.

The trap column is preferably a solid phase extraction (SPE) column, more preferably a SPE cartridge or tip, which is even more preferably disposable. Conventional SPE columns are usable in the invention and the sorbent material may be conventional for the type of analysis being performed, for example a reversed phase resin suitable for samples comprising proteins and/or peptides. The trap column preferably has a generally conical shape having a first open end and a second open end narrower than the first open end. The sorbent preferably sits in the column closer to the second open end than the first open end. In use, a sample is preferably pre-loaded into the trap column, i.e. onto the sorbent, before the robotic system moves the column to the operating position.

The optical sensor is preferably located to sense one or more parameters of the trap column as the trap column is moved between the storage position and the operating position. The optical sensor preferably is for sensing one or more parameters of the trap column prior to flowing solvent through the trap column to the LC column. The optical sensor preferably senses the one or more parameters of the trap column after the trap column has been moved from the storage position, and more preferably before it reaches the operating position, or at the operating position. An alert may be generated by the automated system in response to sensing one or more of the parameters which lie outside a set of predetermined conditions for the parameters and/or the system may take action to prevent an analysis from being performed.

The optical sensor preferably comprises a light source and an optical detector (i.e. light detector). The optical sensor more preferably comprises a light source and an optical detector located to be on opposite sides of the trap column (i.e. in use). In this way, the optical sensor is arranged to detect light that has been transmitted through the trap column. The automated system preferably comprises an outer cover to ensure darkness where the optical detector is located, thereby to shield the optical detector from external light (i.e. the optical detector only detects light from the light source). The detector may be any device for detecting optical signals (i.e. light), e.g. a camera, CCD or photodiode array (preferably a CCD or photodiode array). The optical (light) sensor preferably is a linear optical sensor, i.e. comprising a linear optical detector (such as a linear CCD or linear photodiode array), and more preferably is a linear array sensor, i.e. preferably comprising a linear array optical detector. The linear sensor is preferably able to scan the trap column in lines as the column moves past the sensor, i.e. one line at a time. In other embodiments, the optical sensor may comprise a single pixel light sensor (e.g. a single light sensitive diode). The light source is any suitable light source, preferably a point light source. Light emitting diode (LED) sources are preferred light sources, e.g. an infrared LED. In some embodiments, at least three light sources (e.g. at least three point light sources) are provided in order to determine the position of the trap column in X, Y and Z directions.

The optical sensor preferably is one of an infrared sensor, visible sensor or UV sensor, especially an infrared sensor. In the latter case the light source is an infrared light source and the light detector is an infrared detector, or a broad spectrum detector equipped with an infrared filter. The optical sensor is preferably able to see through the trap column, i.e. sense light that has passed through the trap column. This is generally possible with an infrared sensor and typical trap column materials.

The optical sensor preferably is positioned proximate to the operating position. The system may include two or more optical sensors, which may be positioned adjacent together or at different positions.

Preferably, a computer-based control system is provided for receiving output signals produced by the optical detector and relating them to the parameter of the trap column. Preferably, a computer-based control system is provided to produce an image of the trap column. The computer-based control system is preferably configured to receive the output signals and produce from them an image of the trap column. From the image may be determined the one or more parameters of the trap column. The computer-based control system preferably determines the one or more parameters of the trap column from the image and may, e.g., take action according to pre-determined conditions for the parameters. The action may comprise generating an alert and/or preventing a chromatographic analysis from being performed in response to sensing one or more of the parameters which lie outside a set of pre-determined conditions for the parameters. The computer-based control system may be configured to determine the one or more parameters of the trap column by a process comprising dividing at least part of the image into a plurality of areas (preferably each area comprises a plurality of scan lines) and assigning to each area a darkness value, e.g. determined from grayscale values of pixels in the area. For example, the darkness value for an area may be the sum of the average grayscale value of each of the scan lines in the area. Other measures could be used to determine a darkness value. The darkness values are then indicative of one or more parameters of the trap column. The computer-based control system is also preferably for controlling the robotic system.

The liquid pathway into which the trap column is placed preferably comprises liquid handling components. A liquid delivery member, such as a needle, is preferably provided for engaging with an end of the trap column, more preferably the first open end of the trap column. The liquid delivery member preferably is movable by the robotic system. The liquid delivery member preferably is connected to a supply of solvent which in operation is supplied through the member under pressure from a pump. An adapter or receptacle that is connected to the LC column is preferably provided for engaging with the other end of the trap column, more preferably the second open end of the trap column. The adapter or receptacle is preferably in the form of a funnel, i.e. is of conical shape, into which is positioned the trap column in the operating position. In operation, the trap column is moved to the operating position where it engages with the adapter or receptacle. The liquid delivery member is preferably positioned by the robotic system in the first open end of the trap column and applies mechanical pressure to the trap column to provide a liquid tight seal therewith in the first end. The second open end of the trap column makes a liquid tight seal with the adapter or receptacle connected to the LC column, e.g. by means of the mechanical pressure, such that in operation a solvent is flowed through the liquid delivery member (e.g. under pressure from a pump) and through the trap column to transport sample from the sorbent downstream to the LC column. Thus, the liquid pathway is formed. In some embodiments, the liquid delivery member may be inserted into the first end of the trap column to pick up the column from the storage position and move it to the operating position.

The storage position is preferably provided in a holder such as a storage rack. The rack preferably contains a plurality of storage positions or wells for holding a plurality of trap columns. Typical size racks are 96, 192 or 384 well racks. The robotic system is preferably for moving each trap column in turn from its storage position to the operating position where each trap column is thereby connected in the liquid pathway.

The modes of chromatography are not limited in the invention and, e.g., the LC column may be any suitable type of analytical or preparative (especially analytical) column, especially capillary column, e.g. HPLC, UHPLC, nano-LC column etc. containing any suitable stationary phase. Likewise the solvent may be any suitable type and either gradient or isocratic elution may be used. In view of the preference for SPE trap columns, the invention is useful in SPE-LC, or SPE-LC/MS systems.

BRIEF DESCRIPTION OF THE DRAWINGS

FIG. 5A shows an image obtained from an optical sensor of a trap column in the form of a disposable SPE pipette tip in an embodiment of the invention, where the tip contains no liquid; FIG. 5B shows another image of a disposable tip obtained from an optical sensor, where the tip contains a liquid; and FIG. 5C shows yet another image of a disposable tip obtained from an optical sensor, where the tip is a used tip.

FIG. 6A shows an image obtained from an optical sensor of a disposable SPE pipette tip in an embodiment of the invention showing the centre of the tip end as determined by applying edge detection to the image; and FIG. 6B shows the image of FIG. 6A with part of the image divided into three areas, which are separately analysed to determine parameters of the tip.

DETAILED DESCRIPTION OF EMBODIMENTS

In order to enable more detailed understanding of the invention, but without limiting the scope thereof, various exemplary embodiments of the invention are now described with reference to the accompanying drawings from which further preferred features will be apparent.

Figure 1:
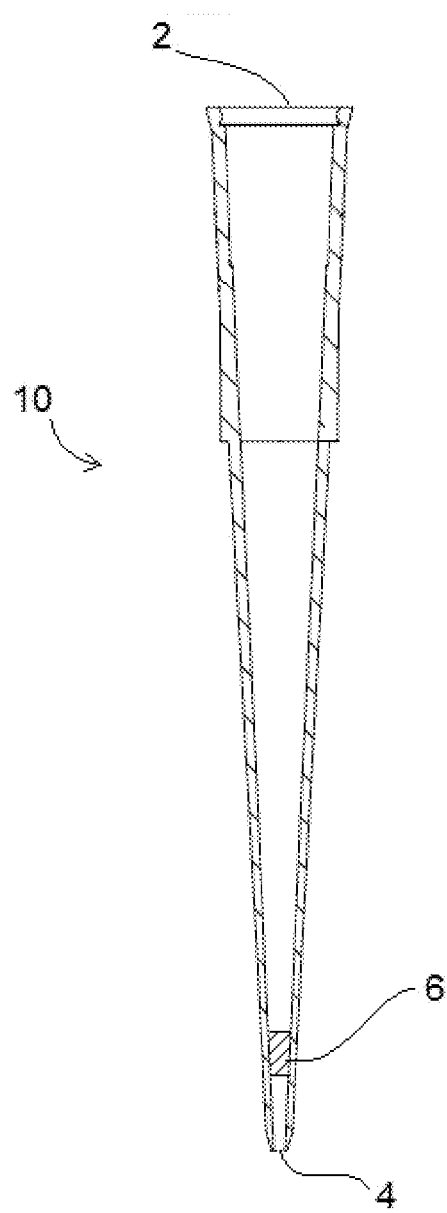
FIG. 1 shows an embodiment of a trap column in the form of a disposable tip, which may be used in the operation of the present invention.

Referring to FIG. 1 there is shown a schematic drawing of an embodiment of a solid phase extraction (SPE) trap column 10 in the form of a disposable pipette tip, which may be used in the operation of the present invention. The example shown is a StageTip™ available from Thermo Scientific™. Whilst the following embodiments are described with reference to the disposable SPE tip, it should be understood that the features of the invention described are applicable to any trap column, especially SPE column. Some preferred features of suitable SPE columns have been described above. The tip is of generally conical shape and has a first open end 2 and a second open end 4 which is narrower than the first open end. The tip is generally made of plastics material, e.g. polypropylene. A sorbent material insert 6 is positioned in the column near the second open end 4. A reversed phase resin is a suitable type of sorbent material for samples comprising proteins and/or peptides for example. Other suitable sorbents are known in the art.

Figure 2:
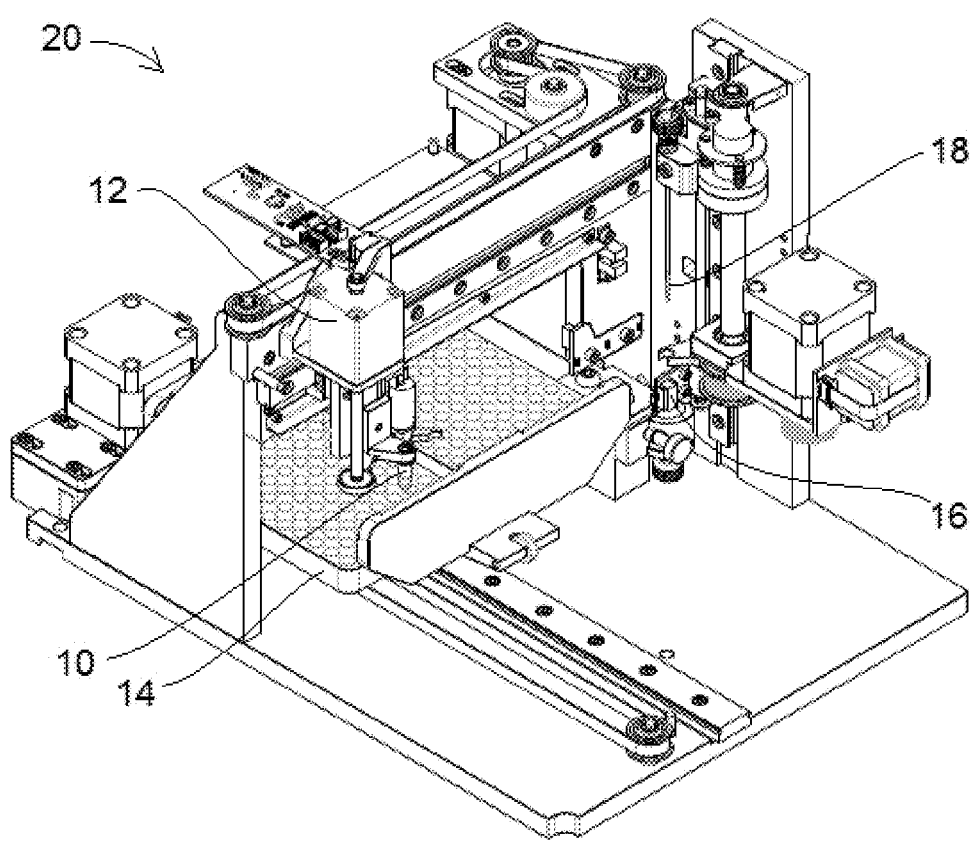
FIG. 2 shows an operation of an embodiment of the present invention.

Referring to FIG. 2 there is shown schematically an operation of an embodiment of the present invention. An automated system 20 comprises a rack 14 housing a plurality of SPE tips 10 in their storage position. The type of rack shown is a 192 well plate. Other common sizes of plate are 96 well and 384 well plates. The tips 10 are of the type shown in FIG. 1. In the described embodiment, the tips in the rack are pre-loaded with sample, e.g. peptide sample. The sorbent material 6 of the tip may be manually loaded with sample prior to positioning in the rack or after positioning in the rack. A robotic system, e.g. such as a pipette handling robot, under the control of a computer-based control system (not shown) picks up a tip 10 from its storage position in the rack using its robotic arm 12 and moves it to the operating position where the end 4 of the tip is inserted by the arm into an opening in an adapter 16, the opening in this embodiment being in the form of a funnel, i.e. of conical shape. The adapter may be made of a suitable polymer material such as, e.g., PEEK. The adapter 16 is connected to an analytical LC column (not shown) located downstream, which may be an HPLC or nano-LC column for instance. Thus, the tip is positioned in its operating position ready for use, i.e. it is positioned in-line with the analytical column. A schematic close up of the tip 10 inserted in the adapter 16 with its conical opening 22 is shown in FIG. 3.

Figure 3:
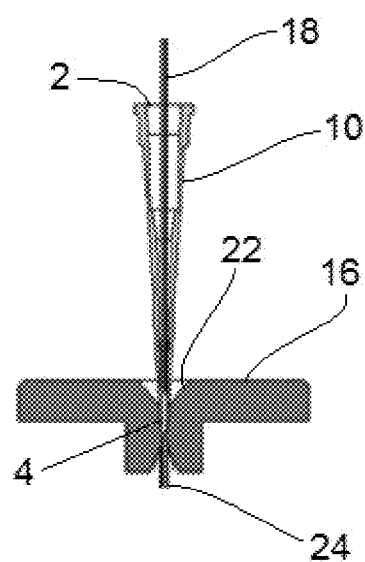
FIG. 3 shows a schematic close up of a trap column in an operating position in an embodiment of the present invention (side cross-section view).

In operation, referring to FIGS. 2 and 3, a stainless steel capillary or needle 18, which is movable by the robotic system up and down, is moved down so that it engages with and fits tight inside the first open end 2 of the tip 10 just above the sorbent material 6 when the tip is positioned in the adapter 16. In other embodiments, it is possible for the system to be modified so that the needle 18 is movable to pick up the tips 10 from the rack and move them to the operating position. The needle 18 acts as a liquid delivery member to deliver solvent under pressure to the tip 10 from a reservoir (not shown) by a piston pump (not shown). Sufficient downward mechanical pressure is applied by the needle 18 so that the needle makes a fluid tight seal against the tip 10 and the tip makes a fluid tight seal against the adapter 16. A capillary tube 24 in the adapter carries solvent to the analytical LC column. In this way, sample (e.g. peptides) is eluted from the tip to the analytical column. A mass spectrometer may be connected downstream of the LC column, e.g. with an electrospray ionisation (ESI) source, for performing LC/MS analysis. After LC or LC/MS analysis, the robotic system withdraws the needle 18 upwards and discards the disposable tip 10. The system is then ready to repeat the operation starting by moving a fresh tip 10 from the rack 14 to the operating position and proceeding as just described.

A problem with such automated systems is that they are not completely reliable and robust. For example, it is possible for the robotic system to fail to pick up a tip, or fail to pick up a tip correctly. In addition, it is possible that a tip that has been picked up may be dropped before it is connected to the LC system. Sometimes the automated system may use a tip that is damaged or otherwise unfit for use, for example since it has already been used. Attempted use of the system when such events occur may cause damage to the system or at least lead to spurious results.

Figure 4:
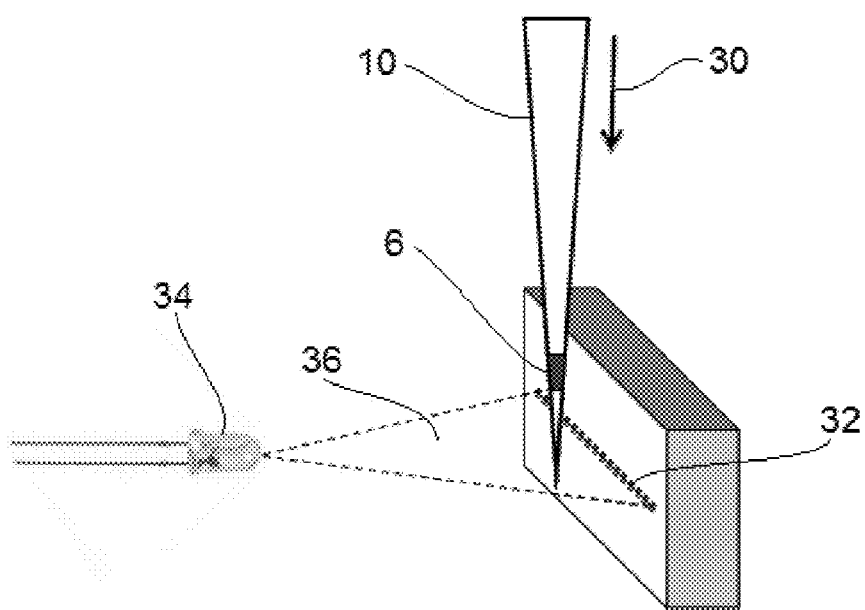
FIG. 4 shows schematically the operating principle of an optical sensor in an embodiment of the present invention.

The present invention addresses such problems by means of features now described with reference to FIG. 4, which shows schematically the operating principle of the invention. In particular, the embodiment employs an optical sensor to sense one or more parameters of the SPE tip before it is used. As described above, the SPE tip 10 is lowered by the robotic system to its operating position as shown by the direction of arrow 30. In proximity to the operating position, i.e. located just above the adapter 16, is a linear optical detector 32 of the optical sensor. In this context the term linear means that the detector extends significantly more in one dimension than the others (e.g. as a line). Here the linear detector extends in a direction substantially perpendicular to the direction of elongation of the SPE tip 10 (which is also the direction of downward movement of the tip towards the adapter). The detector shown is a linear array of photodetectors, i.e. a line of photodetectors. An example of a suitable detector is a 128×1 linear sensor array such as model TSL1401 R (Texas Advanced Optoelectronic Solutions Inc., USA). The TSL1401 R linear sensor array consists of a 128×1 array of photodiodes. The pixels measure 63.5 mm (H) by 55.5 mm (W) with 63.5-mm center-to-center spacing and 8-mm spacing between pixels (400 dots per inch (DPI) sensor pitch). In general, there may be a single line or multiple lines of photodetectors in the optical detector. The single optical detector is thus typically an array detector. A suitable array of photodetectors for the sensor may comprise, for example, a CCD, photodiode array, or other type of pixelated detector. Alternatively, the detector may comprise a single pixel sensor (e.g. just a light sensitive diode). The optical sensor may be, for example, a visible, infrared or ultraviolet sensor, preferably infrared.

In general, there may be more than one optical sensor in the whole system. For example, in addition to the optical sensor 32 in proximity to the adapter 16, there could be at least one other optical sensor positioned elsewhere in the system to inspect the SPE tip 10 at a different position, although one optical sensor has been found to be sufficient for the inspection of SPE tips.

The optical detector 32 in the shown embodiment is located such that it lies on one side of the SPE tip, so that the optical sensor can inspect the tip as the tip moves past the detector. The optical sensor further comprises a light source, in this embodiment comprising an infrared light emitting diode (LED) 34, which is located on the opposite side of the tip 10 to the optical detector 32, to emit light 36 that is sensed by the detector. The detector is thus configured to detect light of one or more wavelengths emitted by the light source, preferably one or more infrared wavelengths. The system is covered by a cover (not shown) to ensure darkness inside so that the detector only senses light from the light source. The arrangement has the advantage that the sensor can effectively see through the tip, i.e. detect light that has been transmitted through the tip. In particular, light from the infrared LED 34 passes through the tip 10, giving a "shadow" image (analogous to an "X-ray image") of the tip at the optical detector. As the tip 10 is moved downwards, the tip is effectively scanned one position at a time (in this case one line at a time) by the linear sensor. In this way, the image of the tip is obtained. From the image, one or more parameters of the tip can be determined, e.g. while it is in the robotic system. Looked at another way, changes in the intensity of the light sensed by the optical sensor as the tip moves past the sensor are indicative of parameters of the tip.

Output signals from the optical detector 32 are received by the computer-based control system to produce the image. The computer-based control system in this embodiment is also configured (i.e. programmed) to analyse the image of the tip so as to determine one or more parameters of the tip, and/or the image of the tip may be analysed manually to determine the parameters. The computer-based control system compares the image to a set of pre-determined conditions for the determined parameters of the tip, the pre-determined conditions being accessible by the computer-based control system, and generate an alert (fault condition) if a defect or fault in the parameters is determined compared to the set of pre-determined conditions. As an example, the alert is one of an Error (e.g. system will not proceed with analysis at least until user intervention) or Warning (e.g. system will proceed with analysis but results should be checked for accuracy). Otherwise the system is determined to be in an OK condition so that the system can proceed with analysis and the user can have confidence in the results.

The parameters of the tip 10 that can be sensed from the image of the tip can include any of the following: the presence or absence of a tip in the robotic arm (e.g. the image may indicate whether a tip has been picked up by the robotic system or not, or has been dropped), the position or orientation of the tip (e.g. whether a tip has been picked up correctly and/or is at the correct orientation), the fluid level in the tip (e.g. water level), the presence and position of a sorbent material in the tip, the condition of the tip material (e.g. whether any damage to the tip is present). These parameters may be sensed before an analysis is performed thereby to avoid possible damage to the system or to avoid obtaining spurious results. This ensures that the system is reliable and robust. Alternatively, the parameters may be assessed after an analysis to decide whether any obtained results from the analysis should be treated as spurious due to the nature of a determined parameter or parameters, e.g. a defect in the parameter(s).

Results have shown that it is possible to clearly see the position of the absorbent material 6 inside the tips 10. It is also possible to detect the waterline (if any) in the tips and to detect if the tips have been used (e.g. whether the absorbent material is pushed downwards in the tip). It is desirable to be able to differentiate between one or more, preferably all, of the following conditions: tip or no tip present; empty tip or tip with material; new or used tip; and liquid or no liquid in the tip.

As an example, the optical sensor placed directly above the adapter for inspecting the tips 10 can make the following checks with the computer-based control system taking the action indicated (generating an Error or Warning alert or fault condition):

Check for presence of Tip
    If tip not present Error
Check for Tip absorbent material 6
    →Warning
Check for dry Tip (check the fluid level, e.g. waterline)
    →Warning
Check for Tip already used (e.g. worn) or material 6 not in the right position
    →Warning
Check for Tip position (has the robotic system misaligned the Tip?)
    →Warning or Error "Error" here means the system will stop and wait for the user to intervene to fix the "problem", e.g. if the tip is not present. "Warning" here means that the tip "looks wrong" and the result cannot be trusted but the instrument will continue the analysis. In a preferred embodiment, all the samples will be electronically labeled with this fault information so that later one can look at the analysis result and compare it with the tip sensor result. Preferably, each of the fault conditions should have a code associated with the particular fault and optionally a score of some sort.

Overall the system has been found to provide a robust means of tip detection based on images from the line sensor.

FIG. 5 shows various images obtained from the optical sensor of different tip scenarios. FIG. 5A shows an image of a trap column in the form of a disposable SPE pipette tip 40, where the tip contains no liquid. The sorbent material is indicated by the darkened area 42 located near the open second end 44 of the tip. FIG. 5B shows another image of a disposable tip 40', where the tip contains water as shown by the light region 46 above the sorbent material indicated by the darkened area 42'. FIG. 5C shows yet another image of a disposable tip 40", where the tip is a used tip as indicated by the dark area 42" representing the sorbent being located further down the tip towards the open second end 44".

In a working example of the present invention, data was obtained in several different test runs each run using one well plate of 96 tips of each tip scenario. The scenarios tested were:

Scenario 1: New Tips, No Liquid
Scenario 2: New Tips, With Liquid
Scenario 3: Used Tips, No Liquid
Scenario 4: Used Tips, With Liquid
Scenario 5: Empty Tips, No Liquid
Scenario 6: Empty Tips, With Liquid
Scenario 7: No Tips present Each scan of a tip took 19 seconds using the LED line sensor to obtain the image. Before analyzing the image, the computer control system subtracted the background (image without tip present). The bottom of the tip (i.e. the second open end) was detected using edge detection and the same was done for the sides of the tip. The center of the bottom of the tip was calculated and saved as coordinates X, Y as shown in FIG. 6A. The example shown in FIGS. 6A and 6B is that of a used tip containing liquid.

To analyze the image, the image was divided into three areas, with nine scan lines used in each area, measured from the detected bottom of the tip. The three areas were named "Used", "Unused", and "Liquid" as shown in FIG. 6B (Used area 52, Unused area 54 and Liquid area 56). If the tip is used, the material is present in the "Used" area and therefore the area 52 will be "dark". If the tip is new, the material is present in the "Unused" area and therefore the area 54 will be dark. If liquid is present on top of the material, the "Liquid" area 56 will be very light.

A "darkness" value was then calculated for each of the three areas. Each "darkness" value is the sum of the average grey scale value of each of the nine scan lines. The edge detection is used to ensure that only pixels within the tip area are used. The darker the pixel, the higher the "darkness" value. An example result is shown below for the tip shown in FIGS. 6A and 6B.

Tip bottom position (X, Y): 87, 4
Darkness Value for "Liquid" area: 916
Darkness Value for "Used" area: 1399
Darkness Value for "Unused" area: 920
Analysis conclusion: Used tip, Liquid present The following pre-determined conditions were used to analyse the image and determine the parameters.

If the Liquid area darkness value <1350, then liquid is present. Then,
    if Used darkness value >1100 and Unused darkness value >1275, the tip is new;
    if Used darkness value >1100 and Unused darkness value <1275, the tip is used;
    if Used darkness value <1100, the tip is empty (no sorbent material).
If Liquid area darkness value >1350, then no liquid is present. Then,
    if Used darkness value <1600 and Unused darkness value >1600, the tip is new;
    if Used darkness value <1600 and Unused darkness value <1600, the tip is empty (no material);
    if Used darkness value >1600, the tip is used.

From the above data for the example in FIGS. 6A and 6B, "Liquid" area: 916; "Used" area: 1399; "Unused" area: 920; applying the above criteria leads to the determination that the tip is a used tip with liquid present.

The optical sensor was tested with all of the seven tip scenarios mentioned above using the 96 tips in the well plate for each scenario and had a very high rate of successfully determining the relevant tip parameters: (i) with liquid or without liquid, and (ii) New or Used tip.

Figure 7A:
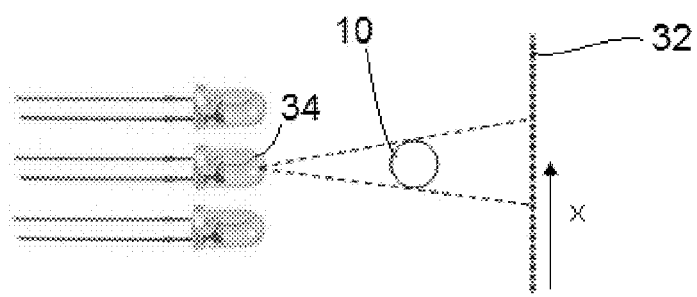
FIGS. 7A and 7B show schematically the operating principle of an optical sensor in a further embodiment of the present invention.
Figure 7B:
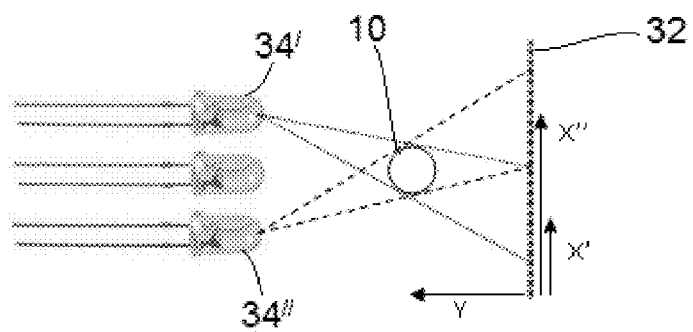

In a further embodiment shown schematically in FIGS. 7A and 7B the optical sensor may also be used to determine the X, Y and Z position of the tip, for example to permit greater accuracy in tip positioning. Thus, not only is the vertical position (Z) determined but also the position of the tip in the horizontal plane (X, Y). For this purpose, the sensor preferably comprises an additional two light sources (at least three light sources in total), in this embodiment three LEDs 34, 34' and 34", once again located on the opposite side of the tip position to the linear optical detector 32. FIGS. 7A and 7B both show views from above of the tip 10 in proximity to the linear optical detector 32. Referring to FIG. 7A, as the tip 10 is lowered to the operating position (not shown) in a direction (Z) into the page, its Z position can be determined as it crosses a line of light from the central LED 34 to the linear optical detector 32. The two additional LEDs 34' and 34" can be used to determine the position of the tip in the horizontal plane. To determine the X position of the tip (i.e. in the direction of elongation of the linear detector), the center LED 34 is illuminated and the X position is determined by calculating the center of the tip shadow on the linear detector 32. To determine the Y position of the tip, the other LEDs are used, one at a time. One of the outer LEDs 34' is illuminated and the distance X' is determined (the distance along X from the edge of the detector to the centre of the tip shadow using the outer LED 34'). Next the other LED 34" is illuminated and the distance X" is determined (the distance along X from the edge of the detector to the centre of the tip shadow using the outer LED 34"). Then the Y distance from the detector can be calculated using simple trigonometry.

The foregoing described embodiments are merely examples of devices according to the invention. It should be understood that various modifications may be made to the shown embodiments whilst still falling within the scope of the appended claims.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. An automated system for handling components of a chromatographic system, comprising:
    a trap column having sorbent material therein;
    a robotic system for moving the trap column from a storage position to an operating position where the trap column is connected in a liquid pathway along which solvent is flowed in operation to a liquid chromatography (LC) column; and
    an optical sensor for sensing one or more parameters of the trap column
    wherein the optical sensor comprises a light source and an optical detector located on opposite sides of the trap column; and wherein the optical sensor can detect light transmitted through the trap column.

2. An automated system as claimed in claim 1, wherein the optical sensor is located to sense the one or more parameters of the trap column as the trap column is moved between the storage position and the operating position.

3. An automated system as claimed in claim 1, wherein the optical sensor is positioned proximate to the operating position.

4. An automated system as claimed in claim 1, wherein the optical sensor comprises a linear array optical detector.

5. An automated system as claimed in claim 4, wherein the linear array optical detector comprises a linear CCD or linear photodiode array.

6. An automated system as claimed in claim 4, wherein the linear array optical detector scans the trap column in lines as the column moves past the sensor.

7. An automated system as claimed in claim 1, wherein the optical sensor comprises an LED light source.

8. An automated system as claimed in claim 7, wherein the LED light source is an infrared LED light source.

9. An automated system as claimed in claim 1, wherein the optical sensor comprises at least three point light sources for determining the position of the trap column in X, Y and Z directions.

10. An automated system as claimed in claim 1, further comprising a computer-based control system for producing an image of the trap column from output signals of an optical detector of the optical sensor.

11. An automated system as claimed in claim 10, wherein the computer-based control system is configured to determine the one or more parameters of the trap column by a process comprising dividing at least part of the image into a plurality of areas and assigning to each area a darkness value determined from grayscale values of pixels in the area.

12. An automated system as claimed in claim 10, wherein the computer-based control system is configured to take action according to pre-determined conditions for the parameters.

13. An automated system as claimed in claim 12, wherein the action includes generating an alert and/or preventing a chromatographic analysis from being performed.

14. An automated system as claimed in claim 10, wherein the computer-based control system is for controlling the robotic system.

15. An automated system as claimed in claim 1, wherein the one or more parameters that can be sensed include any of the following: a presence or absence of a trap column, a position or orientation of the trap column, a fluid level in the trap column, the presence and position of the sorbent material in the trap column, the condition of the trap column and/or whether the trap column is new or used.

16. An automated system as claimed in claim 1, wherein the trap column is a solid phase extraction (SPE) column.

17. An automated system as claimed in claim 1, further comprising: a liquid delivery member for engaging with a first open end of the trap column and an adapter that is connected to the LC column for engaging with a second open end of the trap column, whereby the trap column in the operating position is connected in the liquid pathway with the liquid delivery member positioned by the robotic system in the first end of the trap column and applying mechanical pressure to the trap column to provide a liquid tight seal therewith and the second end of the trap column making a liquid tight seal with the adapter connected to the LC column.

18. A method of automatically handling components of a chromatographic system, comprising:
   using a robotic system to move a trap column having sorbent material therein from a storage position to an operating position where the trap column is connected in a liquid pathway along which solvent is flowed in operation to a liquid chromatography (LC) column; and
   sensing one or more parameters of the trap column using an optical sensor
   wherein the optical sensor comprises a light source and an optical detector located on opposite sides of the trap column; and
   wherein the optical sensor can detect light transmitted through the trap column.

* * * * *